(12) United States Patent
Heck et al.

(10) Patent No.: US 10,420,879 B2
(45) Date of Patent: Sep. 24, 2019

(54) PAIRING A MEDICAL APPARATUS WITH A CONTROL UNIT

(71) Applicant: Roche Diabetes Care, Inc., Indianapolis, IN (US)

(72) Inventors: Wolfgang Heck, Frankenthal (DE); Kai-Oliver Schwenker, HaBloch (DE); Ralf Schmitz, Weinheim (DE); Volker Zeuner, Biblis (DE); Carsten Mueglitz, Schoenau (DE); Thomas Eissenloeffel, Heidelberg (DE); Christian-Alexander Luszick, Ludwigshafen (DE)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 354 days.

(21) Appl. No.: 15/521,320

(22) PCT Filed: Dec. 7, 2015

(86) PCT No.: PCT/IB2015/059400
§ 371 (c)(1),
(2) Date: Apr. 24, 2017

(87) PCT Pub. No.: WO2016/092448
PCT Pub. Date: Jun. 16, 2016

(65) Prior Publication Data
US 2017/0308665 A1    Oct. 26, 2017

(30) Foreign Application Priority Data

Dec. 8, 2014 (EP) .................................. 14196797

(51) Int. Cl.
*A61M 5/142* (2006.01)
*A61B 5/145* (2006.01)
(Continued)

(52) U.S. Cl.
CPC ..... *A61M 5/14244* (2013.01); *A61B 5/14532* (2013.01); *G16H 40/63* (2018.01);
(Continued)

(58) Field of Classification Search
CPC ........ A61M 5/14244; A61M 2205/609; A61M 5/1723; H04W 12/003; H04W 12/00504; H04W 84/18; A61B 5/14532; G16H 40/63
See application file for complete search history.

(56) References Cited

U.S. PATENT DOCUMENTS

| 9,432,361 B2 * | 8/2016 | Mahaffey ............ H04L 63/0853 |
| 2010/0115279 A1 * | 5/2010 | Frikart ................ G06F 19/3418 |
| | | 713/171 |

(Continued)

OTHER PUBLICATIONS

Groce etal., "A New Framework for Efficient Password-Based Authenticated Key Exchange", Oct. 2010, ACM, pp. 516-525. (Year: 2010).*

(Continued)

*Primary Examiner* — Matthew Smithers
(74) *Attorney, Agent, or Firm* — Woodard, Emhardt, Henry, Reeves & Wagner, LLP

(57) ABSTRACT

The invention provides for method of operating a medical instrument (100, 200, 400, 500, 600, 700) comprising a battery powered medical appliance (104) and a control unit (102). Both have Bluetooth communication modules. A first memory of the medical appliance contains a onetime password (210) and of a password-authenticated key agreement algorithm (212). The control unit has a second memory (223) with an implementation of the password-authenticated key agreement algorithm (212'). The method comprises entering (300) the onetime password into the data entry interface (140, 221, 504, 604) of the control unit. The method further comprises generating (302) a Bluetooth (Continued)

encryption key (218) by the medical appliance and the control unit with the onetime password by exchanging data across the wireless communication channel by executing the password-authenticated key agreement algorithm. The method further comprises storing (304) the Bluetooth encryption key in the first memory. The method further comprises disabling (306) the password-authenticated key agreement algorithm in the first memory after storing the Bluetooth encryption key in the first memory. The method further comprises storing (308) the Bluetooth encryption key in the second memory. The method further comprises establishing (310) an encrypted Bluetooth communication channel using the first Bluetooth communication module and the second Bluetooth communication module. The encrypted Bluetooth communication channel is the wireless communication channel encrypted using the Bluetooth encryption key.

21 Claims, 9 Drawing Sheets

(51) Int. Cl.
*G16H 40/63* (2018.01)
*H04W 12/00* (2009.01)
*A61M 5/172* (2006.01)
*H04W 84/18* (2009.01)

(52) U.S. Cl.
CPC ........ *H04W 12/003* (2019.01); *A61M 5/1723* (2013.01); *A61M 2205/609* (2013.01); *H04W 12/00504* (2019.01); *H04W 84/18* (2013.01)

(56) References Cited

U.S. PATENT DOCUMENTS

| | | | | |
|---|---|---|---|---|
| 2014/0281547 | A1* | 9/2014 | Modzelewski | H04L 63/061 713/171 |
| 2014/0298022 | A1* | 10/2014 | Proennecke | G06F 9/455 713/168 |
| 2015/0147970 | A1* | 5/2015 | Tan | H04W 12/08 455/41.2 |
| 2015/0207626 | A1* | 7/2015 | Neftel | G08C 17/02 713/168 |

OTHER PUBLICATIONS

Katz et al., "Efficient and Secure Authenticated Key Exchange Using Weak Passwords", Nov. 2009, ACM, pp. 1-39. (Year: 2009).*
International Application No. PCT/IB2015/059400 International Search Report and Written Opinion, dated Jun. 20, 2017.

* cited by examiner

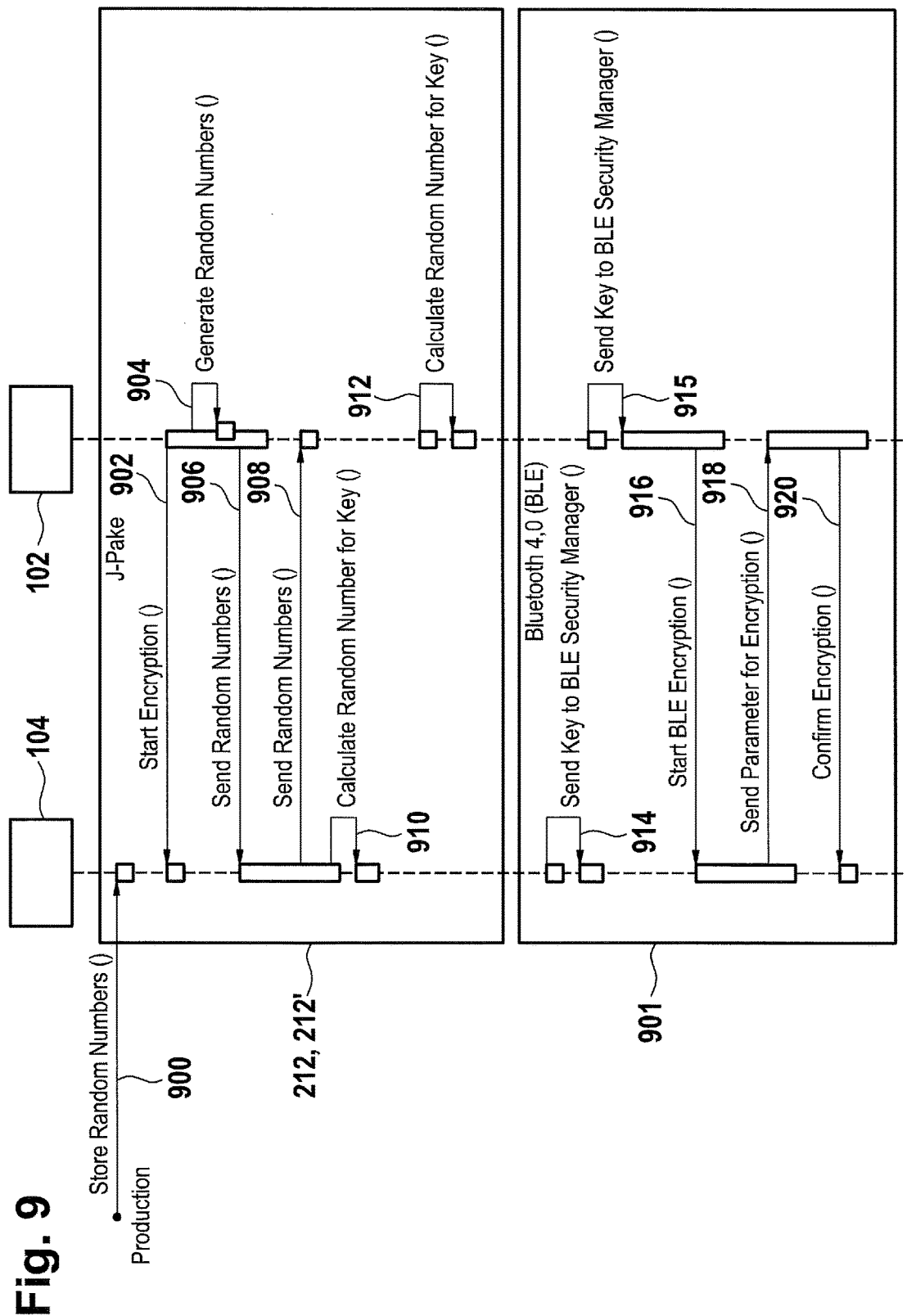

PAIRING A MEDICAL APPARATUS WITH A CONTROL UNIT

FIELD OF THE INVENTION

The invention relates to medical instruments for monitoring and maintaining a subjects blood sugar level.

BACKGROUND AND RELATED ART

So called patch insulin pumps and glucose monitors are attached to the surface of a subject. It is advantageous to minimize the weight of these pumps and monitors by using a control unit that is separate from the portion attached to the subject. If a wireless connection is made between the portion attached to the subject and the control unit it is critical that the connection be secure and impervious to attacks. Losing control of an insulin pump to a hacker could endanger the health of the person wearing the pump.

SUMMARY

The invention relates to a method of operating a medical instrument and a medical instrument in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, touchscreen, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

In one aspect the invention relates to a method of operating a medical instrument. The medical instrument comprises a medical appliance and a control unit. The medical appliance is powered by a first battery. The control unit is powered by a second battery. The medical appliance comprises an electronic portion and a subcutaneous portion. The subcutaneous portion may include such things as a cannula for attaching to a pump for pumping a fluid into a subject. The subcutaneous portion may also include a sensor which may be inserted into a subject. The electronic portion comprises a first processor and a first memory. The first memory contains a onetime password.

A onetime password encompasses a password which may one be used or is intended to be used a single time. The onetime password stored in the first memory is prevented from being used again after Bluetooth encryption key is stored in the first memory, because the password-authenticated key agreement algorithm. is disabled. In this context, the onetime password means that the onetime password can only be used for pairing the medical device once. The term onetime is therefore considered to be descriptive of how the password is used. The term "onetime password" may be considered equivalent and/or with the term "single use password" or "password" herein.

The first memory further comprises an implementation of a password-authenticated key agreement algorithm.

The implementation of the password-authenticated key agreement algorithm may be executed or is in the form of machine-executable instructions for execution by the first processor.

The control unit comprises a second processor and a second memory. The control unit comprises a data entry interface. The second memory contains the implementation of the password-authenticated key agreement algorithm. The implementation of the password-authenticated key agreement algorithm in the second memory is in a machine-executable form for execution by the second processor. The password-authenticated key agreement algorithm in the first and second memory are complimentary. In other words the implementation of the password-authenticated key agreement algorithm in the first memory is a first portion of the algorithm. The implementation of the password-authenticated key agreement algorithm in the second memory is a second portion of the password-authenticated key agreement algorithm. The first and the second portions of the password-authenticated key agreement algorithm work together such that the first processor and the second processor execute the password-authenticated key agreement algorithm with each other.

The medical appliance comprises a first Bluetooth communication module. The control unit further comprises a second Bluetooth communication module. The first Bluetooth communication module and the second Bluetooth communication module are operable for forming a wireless communication channel between the medical apparatus and the control unit.

The method comprises the step of entering the onetime password into the data entry interface. This step may take different forms. For example if the data entry interface is a keypad a user may simply type the onetime password into the data entry interface. In other examples, the data entry interface may be a variety of other types of interfaces or readers for receiving data. For example the data entry interface may comprise an optical, acoustic, or radio-frequency system for receiving the onetime password.

The method further comprises the step of generating a Bluetooth encryption key by the medical appliance and the control unit with the onetime password by exchanging data across the wireless communication channel by executing the password-authenticated key agreement algorithm. The control unit initiates execution of the password-authenticated key agreement algorithm. The onetime password is used as a shared secret by the password-authenticated key agreement algorithm to generate the Bluetooth encryption key. The use of the onetime password as a shared secret prevents so-called man-in-the-middle attacks.

The method further comprises the step of storing the Bluetooth encryption key in the first memory. The method further comprises the step of disabling the password-authenticated key agreement algorithm in the first memory after storing the Bluetooth encryption key in the first memory. Once the password-authenticated key agreement algorithm has been executed once to generate the Bluetooth encryption key the medical instrument is no longer able to execute the password-authenticated key agreement algorithm any longer. This prevents the medical appliance from pairing with any other device except the control unit. The method further comprises the step of storing the Bluetooth encryption key in the second memory. The method further comprises the step of establishing an encrypted Bluetooth communication channel using the first Bluetooth communication module and a second Bluetooth communication module. The encrypted Bluetooth communication channel is encrypted using the Bluetooth encryption key.

By using the onetime password as a shared secret the password-authenticated key agreement algorithm can be used by the medical instrument and the control unit to establish a Bluetooth encryption key securely. The shared secret is shared outside of the wireless communication channel formed by the Bluetooth communication modules. This may greatly increase the security and reduce the risk that the medical appliance can be taken over or controlled by anything but the control unit.

Since the medical appliance is disabled from repeating the password-authenticated key agreement algorithm the paring of the medical appliance with a control unit can only happen once. If the medical appliance and the control unit lose their connection, they can repair using the Bluetooth encryption key again.

In another embodiment, the password-authenticated key agreement algorithm is a J-PAKE algorithm. The J-PAKE algorithm may also be referred to herein as a password-authenticated key agreement algorithm. A J-PAKE algorithm or protocol is a type of password-authenticated key agreement protocol that enables two parties to establish private and authenticated communication solely based on their shared (low-entropy) password without requiring the use of a Public Key Infrastructure. The use of a J-PAKE algorithm provides for added security and eliminates the possibility of a man in the middle attack without a complicated Public Key Infrastructure.

Some embodiments may provide for improved security of the pairing between the medical appliance and the control unit. In particular, the combination of using a J-PAKE algorithm for pairing and then disabling the J-PAKE algorithm in the first memory causes the onetime password to be functional for paring only once without the use of a external server or system for managing keys. The use of the J-PAKE algorithm also prevents any sort of man in the middle attack.

In another embodiment, the subcutaneous portion comprises a glucose sensor (130). The medical appliance comprises a continuous glucose monitoring system (126,130). The method comprises the step of recording a glucose measurement using the continuous glucose monitoring system. The method further comprises the step of transferring the glucose measurement to the control unit using the encrypted Bluetooth communication channel.

In another embodiment, the subcutaneous portion comprises at least one cannula (124). The medical appliance comprises a pumping system (122). The pumping system comprises anyone one of the following: a insulin pump for pumping insulin through the at least one cannula, a glucagon pump for pumping glucagon through the at least one cannula, and combinations thereof. The method further comprises the step of controlling the pumping system via the encrypted Bluetooth communication channel by the control unit.

In another embodiment, the password-authenticated key agreement algorithm is a J-PAKE algorithm.

In another embodiment, the disabling the password-authenticated key agreement algorithm in the first memory comprises preventing execution the password-authenticated key agreement algorithm by the first processor after the Bluetooth encryption key has been stored in the first memory.

In some examples, this could be accomplished for example by first machine executable instructions in the first memory containing commands that prevent execution of the password-authenticated key agreement algorithm after the Bluetooth encryption key is stored in the first memory. These first machine instructions or even the implementation of the password-authenticated key agreement algorithm its self could be modified such that all or a portion of the password-authenticated key agreement algorithm in the first memory is deleted or overwritten. This would make it impossible to induce the medical appliance to go through the Bluetooth pairing process a second time, even if the device were hacked.

In another embodiment, the disabling the J-PAKE algorithm in the first memory comprises preventing execution of the J-PAKE algorithm by the first processor after the Bluetooth encryption key has been stored in the first memory.

In some examples, this could be accomplished for example by first machine executable instructions in the first memory containing commands that prevent execution of the J-PAKE algorithm after the Bluetooth encryption key is stored in the first memory. These first machine instructions or even the implementation of the J-PAKE algorithm its self could be modified such that all or a portion of the J-PAKE algorithm in the first memory is deleted or overwritten. This would make it impossible to induce the medical appliance to go through the Bluetooth pairing process a second time, even if the device were hacked.

In another embodiment the password-authenticated key agreement algorithm is an EKE algorithm.

In another embodiment, the password-authenticated key agreement algorithm is a PPK algorithm.

In another embodiment, the password-authenticated key agreement algorithm is a SPEKE algorithm.

In another embodiment, the password-authenticated key agreement algorithm is a Dragonfly algorithm.

In another embodiment, the password-authenticated key agreement algorithm is compliant with the IEEE standard 802.11-2012.

In another embodiment, the electronic system has an exterior surface. The medical appliance may also be referred to as an electronic system herein. The exterior surface comprises a label with password data. The password data is descriptive of the onetime password. In some instances the password data may be identical with the onetime password. In other examples the password data may comprise data which can be transformed into the onetime password. For example when the password data is passed through a hash function it may be hashed into the appropriate password. The password data may also be a machine-readable code which may be transformed into the password. In another example the password data comprises also the serial number of the medical appliance. In some instances the onetime password and the serial number are in the password data. In some instances the onetime password is or comprises the serial number of the medical appliance.

In another embodiment, the data entry interface comprises a keypad. The method further comprises the step of entering the onetime password and/or the password data using the keypad. For example if the control unit has a touch screen the method may comprise displaying the keypad on the touch screen such that the step of entering the onetime password using the touch screen can be completed.

In another embodiment the medical instrument further comprises printed matter comprising the onetime password. The printed matter may for instance be a piece of paper which is included with the medical appliance which contains such things as the onetime password and/or the serial number of the medical appliance.

In another embodiment, the label is machine-readable. The data entry interface is an optical label reader configured for reading the password data. The optical label reader may take different forms depending upon the different type of label. In some instances the optical label reader is a camera. In other instances such things as a laser scanner may be used. The step of entering the onetime password into the data entry interface comprises reading the password data with the optical label reader. The step of entering the onetime password into the data entry interface further comprises transforming the password data into the onetime password. For example if the label contains the onetime password and the serial number this step may include extracting the onetime password from the optical reader information or data.

In another embodiment, the password data is encoded as a barcode and the optical label reader is a barcode reader.

In another embodiment, the password data is encoded as an EAN code and the optical label reader is an EAN code reader.

In another embodiment, the password data is encoded as a two-dimensional optical code and the optical label reader is a two-dimensional optical code reader.

In another embodiment, the password data is encoded as a QR code and the optical label reader is a QR code reader.

In another embodiment, the password data is encoded as a data matrix code and the optical label reader is a data matrix code reader.

In the above examples for example the barcode reader, the EAN code reader, the two-dimensional optical code reader, and the QR code reader may be implemented in some examples as a camera with appropriate software for analyzing pictures taken by the camera.

In another embodiment, the optical label reader is a digital camera.

In another embodiment, the electronic portion comprises an optical indicator. The optical indicator in one example may be a light or light emitting diode which can flash. The data entry interface comprises an optical detector. The optical detector may for instance be a digital camera or it may be another detector for detecting signals from the optical indicator. In some examples the optical indicator and optical detector could be operational for operating in the infrared or ultraviolet range. The step of entering the onetime password into the data entry interface comprises transmitting the onetime password using the optical indicator. The step of entering the onetime password into the data entry interface further comprises receiving the onetime password using the optical detector.

In another embodiment, the electronic portion comprises an audio signal generator. The audio signal generator may for instance be a speaker, piezo transducer or other transducer used to generate audio sounds. The data entry interface comprises an audio signal detector. The audio signal detector for instance may be a microphone. The step of entering the onetime password into the data entry interface comprises transmitting the onetime password using the audio signal generator. The step of entering the onetime password into the data entry interface further comprises receiving the onetime password using the audio signal generator.

For example, the audio signal generator could use one or multiple tones for transmitting the data. For example a single frequency of around 3 kHz may be useful. In this case amplitude modification of the audio signal could be performed. If a second or more frequencies are used one of the frequencies could be used as a clock signal. This may enable more rapid transmitting of the data.

In another embodiment, the medical appliance has a switch which starts the medical appliance to transmit the onetime password.

In another embodiment, the electronic portion comprises a first RFID module. The data entry interface is a second RFID module. The step of entering the onetime password into the data entry interface comprises exchanging the onetime password using the first RFID module and the second RFID module. The use of the RFID module may be useful because RFID has a shorter range than Bluetooth. Also the use of two different communication protocols may reduce the chances of the onetime password being stolen and the method being circumvented.

In another embodiment the first RFID module is controlled by the first processor.

In another embodiment, the first RFID module is an RFID tag. For example the RFID tag could be mounted internally or on an external surface of the medical appliance. In some instances the RFID tag may also combine a machine-readable label. The RFID tag comprises an RFID tag memory and the RFID tag memory contains the onetime password. In this case the first memory and the RFID tag memory both contain the onetime password. Use of an RFID tag attached to the medical appliance may be useful because the user could for instance remove and/or destroy the RFID tag after its use.

In another embodiment, the electronic portion comprises a first NFC module. The data entry interface is a second NFC module. The step of entering the password data into the data entry interface comprises exchanging the password data using the first NFC module and the second NFC module.

In another embodiment, the medical appliance comprises an insulin pump.

In another embodiment, the medical appliance comprises a glucagon pump.

In another embodiment, the medical appliance comprises a continuous glucose monitoring system.

In another embodiment, the control unit is a mobile telephone device or a tablet computer.

In another embodiment, the onetime password has a lower entropy than the Bluetooth encryption key.

In another embodiment, the step of entering the onetime password into the data entry interface comprises: entering password data into the data entry interface, wherein the password data is descriptive of the onetime password; and transforming the password data into the onetime password.

In another aspect, the invention provides for a medical instrument. The medical instrument comprises a medical appliance and a control unit. The medical appliance is battery-powered by a first battery. The control unit is battery-powered by a second battery. The medical appliance comprises an electronic portion and a subcutaneous portion. The electronic portion comprises a first processor and a first memory. The first memory contains a onetime password. The first memory further contains an implementation of a password-authenticated key agreement algorithm. The first memory further contains the first machine-executable instructions. The control unit comprises a second processor and a second memory. The control unit comprises a data entry interface.

The second memory contains the implementation of the password-authenticated key agreement algorithm. The second memory further contains second machine-executable instructions. The medical appliance comprises a first Bluetooth communication module. The control unit further comprises a second Bluetooth communication module. The first Bluetooth communication module and the second Bluetooth communication module are operable for forming a wireless communication channel between the medical appliance and the control unit. Execution of the second machine-executable instructions causes the second processor to receive the onetime password into the data entry interface.

In some examples, execution of the first machine-executable instructions may cause the first processor to transmit the onetime password to the data entry interface. For example if the medical appliance transmits the onetime password via sound, light, image or radio waves. Execution of the second machine-executable instructions and the first machine-executable instructions cause the first processor and the second processor to generate a Bluetooth encryption key by the medical appliance and the control unit with the onetime password by exchanging data across the wireless communication channel by executing the password-authenticated key agreement algorithm.

The control unit initiates execution of the password-authenticated key agreement algorithm. Execution of the first machine-executable instructions causes the first processor to store the Bluetooth encryption key in the first memory. Execution of the first instructions further causes the first processor to disable the password-authenticated key agreement algorithm in the first memory after storing the Bluetooth encryption key in the first memory. Execution of the second machine-executable instructions further cause the second processor to store the Bluetooth encryption key in the second memory. Execution of the second machine-executable instructions and the first machine-executable instructions cause the first processor and the second processor to establish an encrypted Bluetooth communication channel using the first Bluetooth communication module and the second Bluetooth communication module. The encrypted Bluetooth communication channel is encrypted using the Bluetooth encryption key.

It is understood that one or more of the aforementioned embodiments of the invention may be combined as long as the combined embodiments are not mutually exclusive.

BRIEF DESCRIPTION OF THE DRAWINGS

In the following embodiments of the invention are explained in greater detail, by way of example only, making reference to the drawings in which:

FIG. 9 shows a flow chart which illustrates a method using the J-PAKE algorithm to generate Bluetooth security keys.

DETAILED DESCRIPTION

Like numbered elements in these figures are either equivalent elements or perform the same function. Elements which have been discussed previously will not necessarily be discussed in later figures if the function is equivalent.

Figure 1:
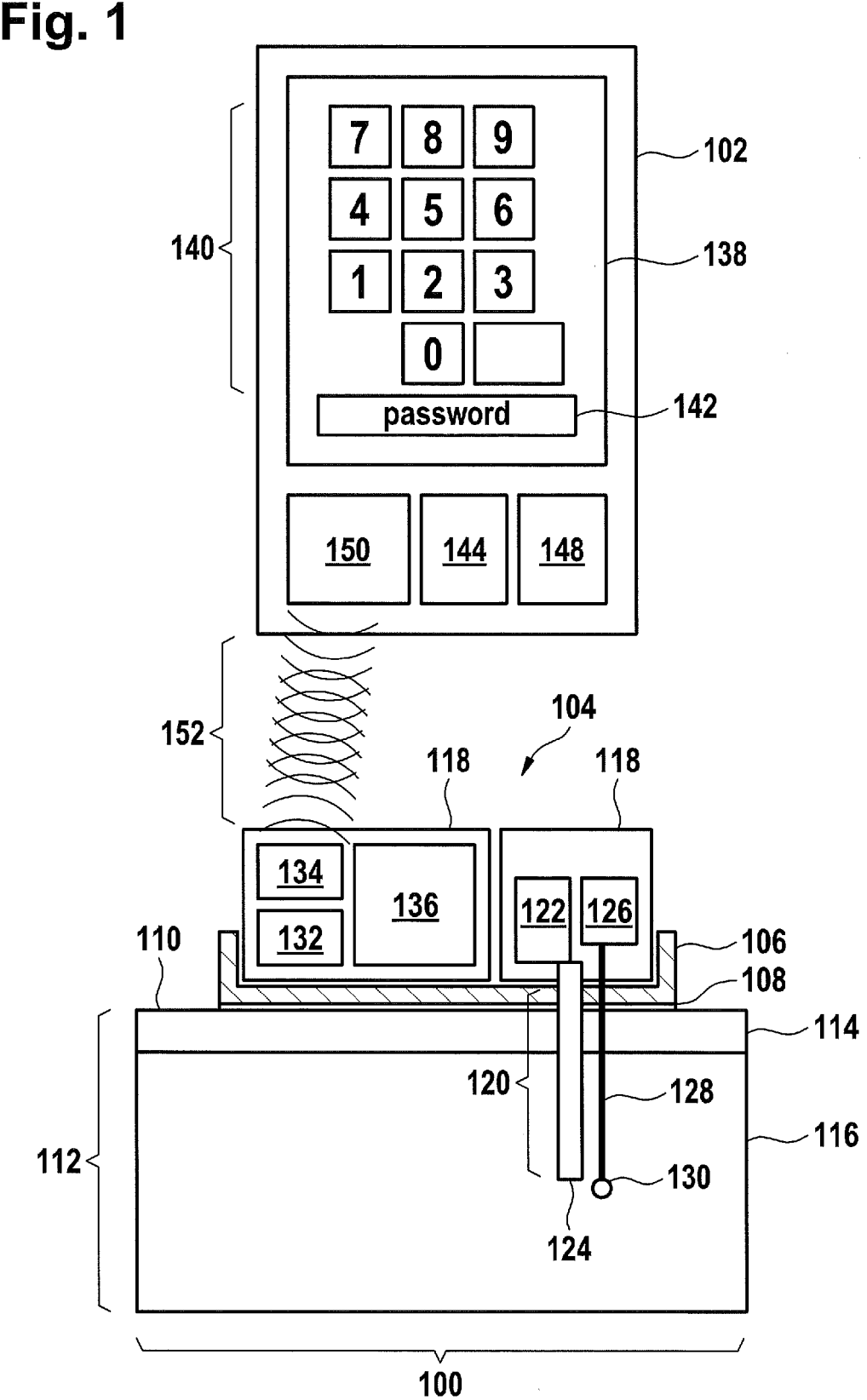
FIG. 1 illustrates an example of a medical instrument.

FIG. 1 shows an example of a medical instrument 100. The medical instrument comprises a control unit 102 and a medical appliance 104. The medical appliance 104 is shown as being in a cradle 106 that has an adhesive layer 108 that attaches it to the outside layer 110 of a subject 112. The view of the subject 112 is cross-sectional. The exterior surface 110 is shown as being in contact with a dermis or skin layer 114. The dermis is in contact with fatty tissue 116. The medical appliance 104 is shown as having an electronic portion 118 and a subcutaneous portion 120. The subcutaneous portion comprises a cannula 124 and a sensor 130 attached to a sensor lead 128. In this example the electronic portion 118 contains a pump 122 which is connected to the cannula 124 that extends into the fatty tissue 116. For example the pump 122 could be used to dispense insulin and/or glucagon. In some instances there may be more than one pump so that both insulin and glucagon can both be dispensed. The electronic portion 118 is further shown as having a sensor controller 126 that is connected to the sensor lead 128 that extends into the subject 112. The sensor 130 could for example be a glucose sensor for a continuous glucose monitoring system.

The electronic portion 118 is shown additionally comprising a first processor 132, a first Bluetooth communication module 134 and a first battery 136. In FIG. 1 not all components of the control unit 102 and the medical appliance 104 are shown.

The control unit 102 is shown as having a touch screen 138. On the touch screen 138 is implemented a touchpad 140. For example, the touchpad 140 could be used for inputting the onetime password. The touch screen 138 could also have other elements such as a box or display element 142 for showing data that was typed. Not all components of the control unit 102 are shown in this Fig. The control unit 102 is shown as further comprising a second processor 144 that is powered by a second battery 148. The control unit 102 further comprises a second Bluetooth module 150 that is used to form a wireless communication channel 152 between the control unit 102 and the medical appliance 104. The control unit 102 can then send and receive data via the wireless communication channel 152 to control and/or monitor the operation of the medical appliance 104.

Figure 2:
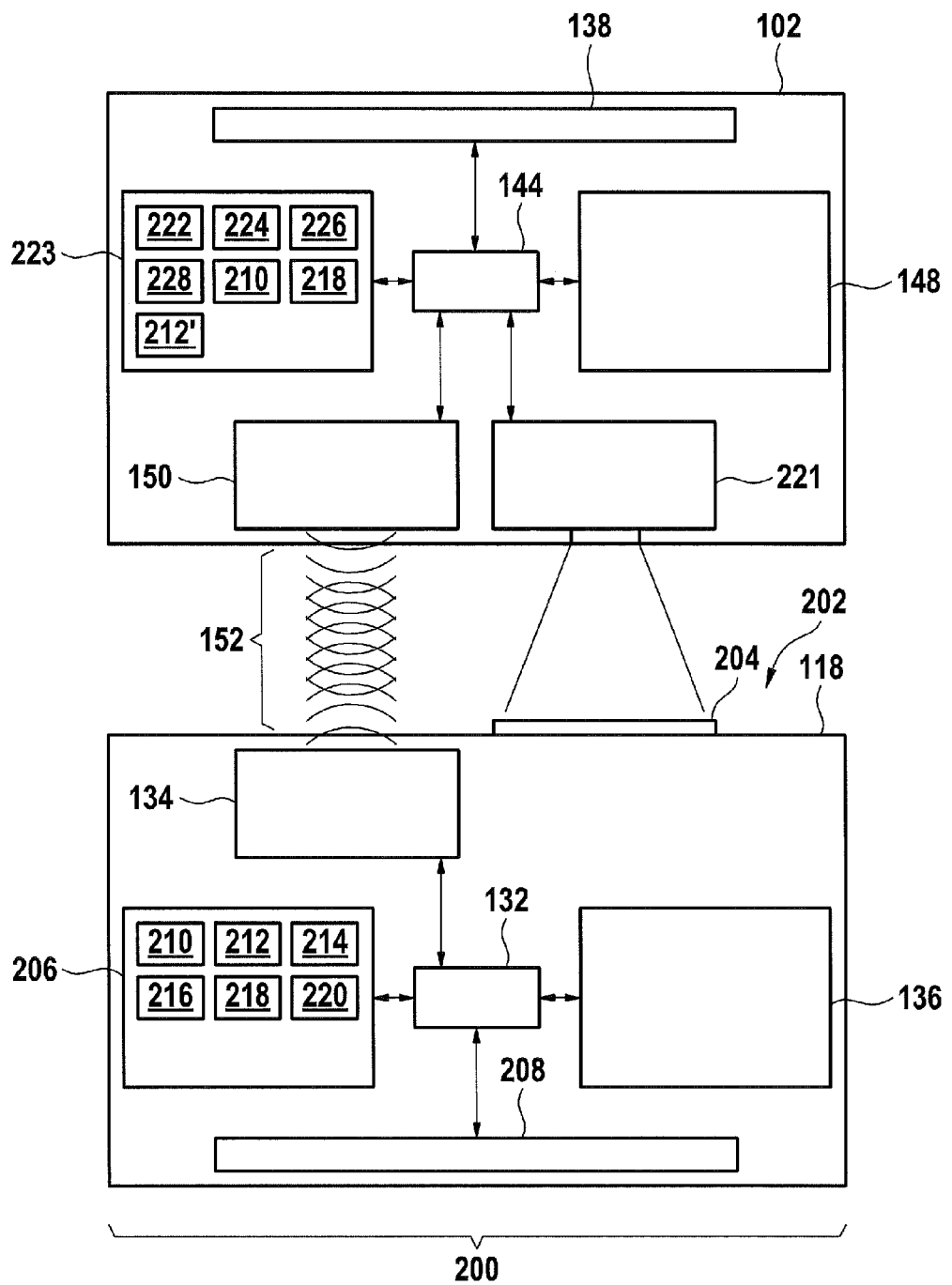
FIG. 2 illustrates a further example of a medical instrument.

FIG. 2 shows a further example of medical instrument 200. The medical instrument 200 has an exterior surface 202 to which a machine-readable label 204 is attached. The machine-readable label 204 may encode password data that is descriptive or can be used to derive the onetime password. In this example the electronic portion 118 is further shown as containing a first memory 206 and a hardware interface 208. The hardware interface 208 enables the processor 132 to control the operation and function of the components of the medical appliance. Not all components are shown in FIG. 2.

The first memory 206 is shown as having a onetime password 210 stored within it. The first memory 206 is shown as further containing a password-authenticated key agreement algorithm 212. The first memory 206 is further shown as containing a control module 214 which provides code which enables the processor 132 to control the operation and function of the entire medical apparatus. The first memory 206 is further shown as containing a data log 216. The data log contains data which may be generated or stored as the processor 132 implements the control module 214. For instance how the pump 122 or sensor data 130 may be stored in this file. The first memory 206 is further shown as containing a Bluetooth encryption key 218 that was derived upon executing the password-authenticated key agreement algorithm 212. The first memory 206 is further shown as containing instructions from the control unit 220 that are received via the wireless communication channel 152.

In this particular example the control unit 102 is shown as further comprising a camera 221 and a second memory 223. The camera 221 is shown as being positioned so that it can take an image of the machine-readable label 204. The second memory 223 is shown as containing an operating system 222 which provides the operating system for the control unit 102. For instance the operating system 222 may be android, iOS, LINUX, or other operating system. The second memory 223 is further shown as containing a control application 224 that enables the processor 144 to control the medical appliance 104 via the wireless communication channel 152. The camera 221 may be used to take an image of the machine-readable label 204. The second memory 223 is shown as containing in this case an image which is identified as password data 226. The second memory 223 is shown as further containing a password transformation module 228 which enables the processor 114 to decode the password data or image 226 into the onetime password 210. The computer memory 223 is further shown as containing an implementation of the password-authenticated key agreement algorithm 212'. The machine-executable instructions 212 and 212' enable the control unit 102 and the medical appliance 104 to generate the Bluetooth encryption key 218 using the onetime password 210 as a shared secret. The features of FIG. 1 and FIG. 2 may be combined. In the example shown in FIG. 2 once the camera 221 has taken an image of the machine-readable label 204 this may initiate the implementation of the password-authenticated key agreement algorithm.

Figure 3:
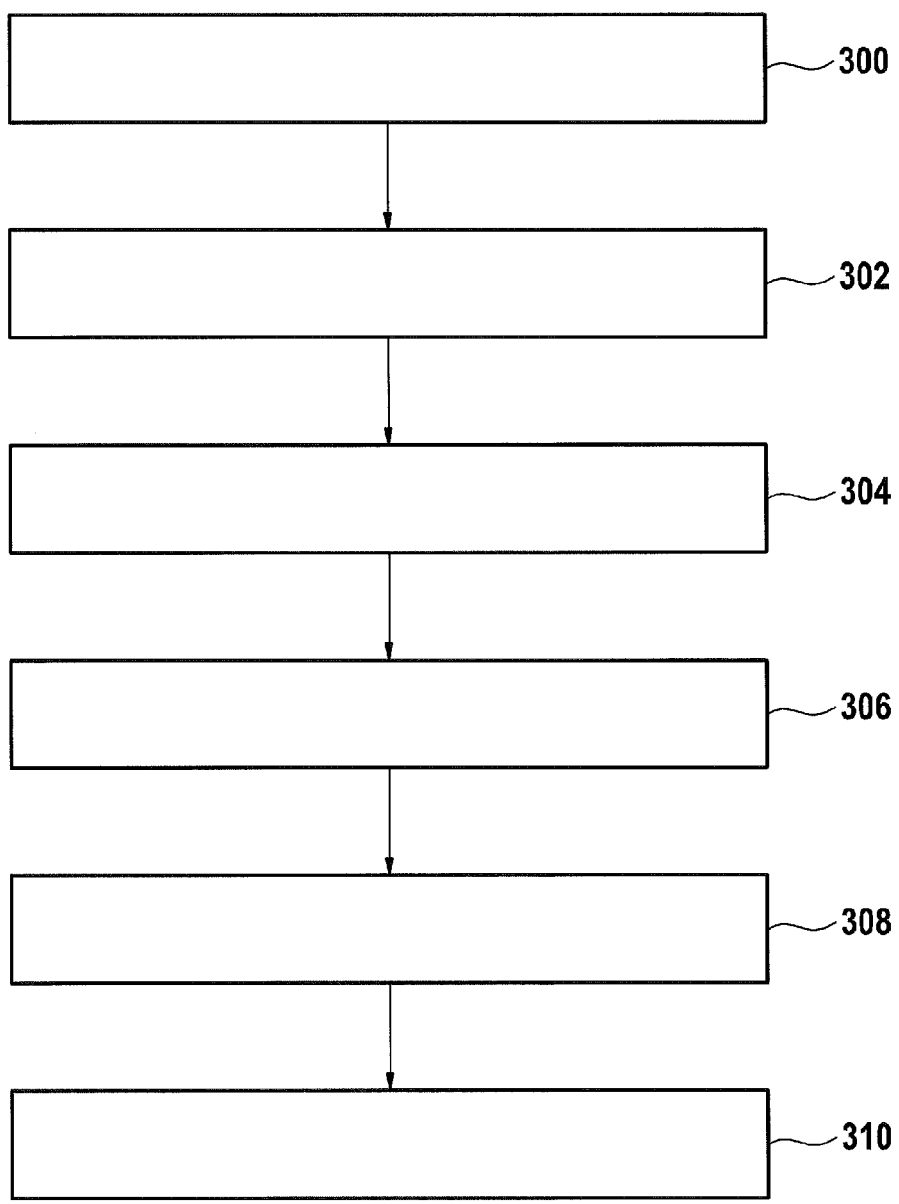
FIG. 3 shows a flow chart which illustrates and example of a method of operating a medical instrument.

FIG. 3 shows an example of a method illustrated in a flowchart which shows how a medical instrument according to an example may be operated. First in step 300 the onetime password 210 is entered into the data entry interface 140. This step may also be provided by using the camera 221 or other examples which follow in later Figs. Next in step 302 a Bluetooth encryption key 218 is generated by the medical appliance 104 and the control unit 102 by exchanging data across the wireless communication channel 152. This is done by executing the password-authenticated key agreement algorithm 212, 212' the control unit 102 initiates the execution of the password-authenticated key agreement algorithm 212, 212'.

Next in step 304 the Bluetooth encryption key 218 is stored in the first memory 206. The next step is step 306 where the password-authenticated key agreement algorithm 212 is disabled after storing the Bluetooth encryption key 218 in the first memory 206. Next in step 308 the Bluetooth encryption key 218 is stored in the second memory 223. Finally in step 310 an encrypted Bluetooth communication channel 152 is established using the first Bluetooth communication module 134 and the second Bluetooth communication module 150. The Bluetooth communication channel is the wireless communication channel 152 that has been encrypted using the Bluetooth encryption key 218.

Figure 4:
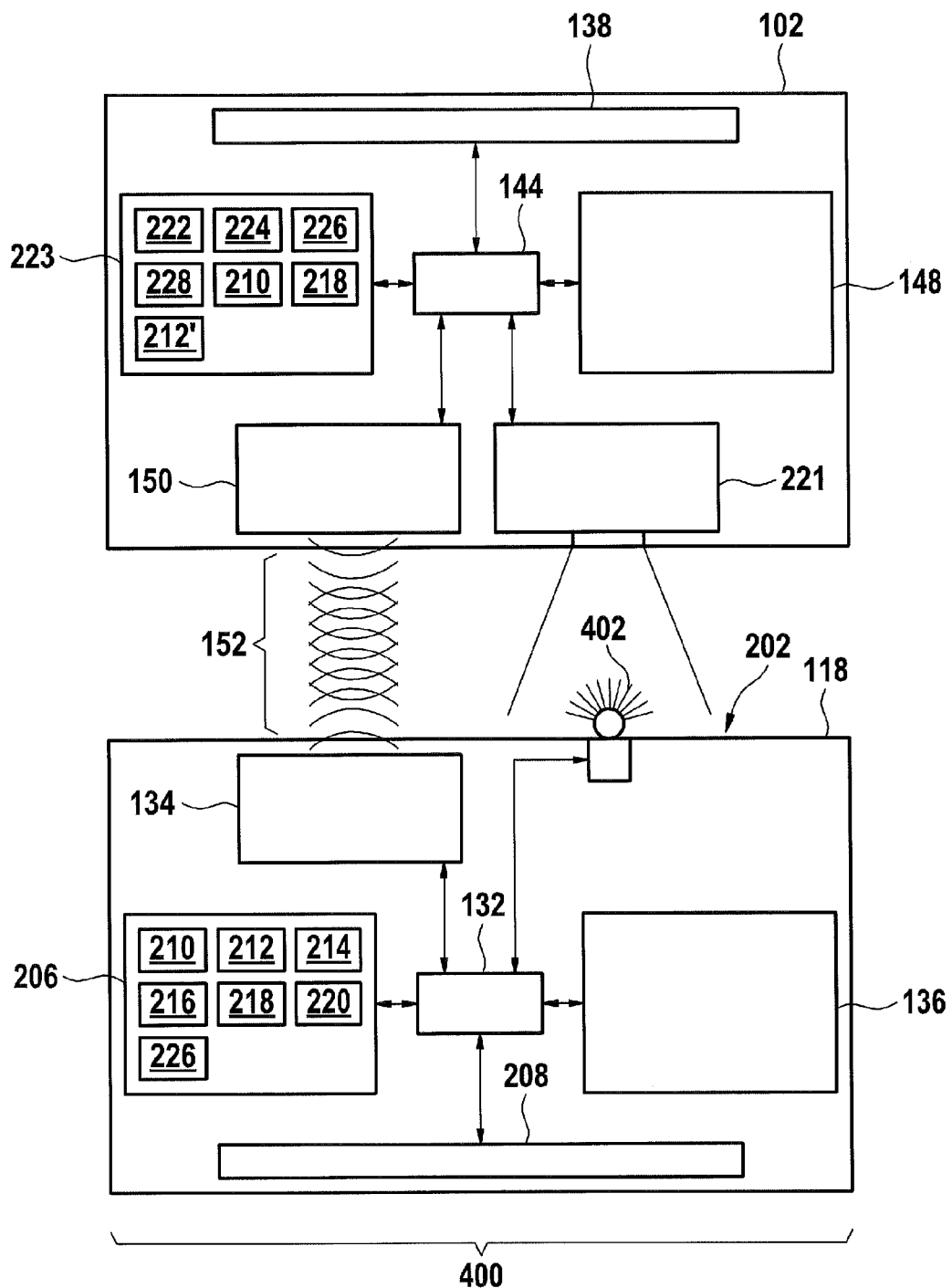
FIG. 4 illustrates a further example of a medical instrument.

FIG. 4 shows a further example of the medical apparatus 400. In this example instead of having a label 204 there is a light source or light 402 which is exposed to the outside surface 202 or visible when viewing outside surface 202. The first memory 206 contains the password data 226. In this case the password data 226 is the untimed password 210 encoded as pulses for the light 402. The processor 132 then controls the light 402 to blink according to the password data 226. The camera 221 then records these pulses and records it as the password data 226. Other types of optical detectors 221 could be substituted for the camera 221.

Figure 5:
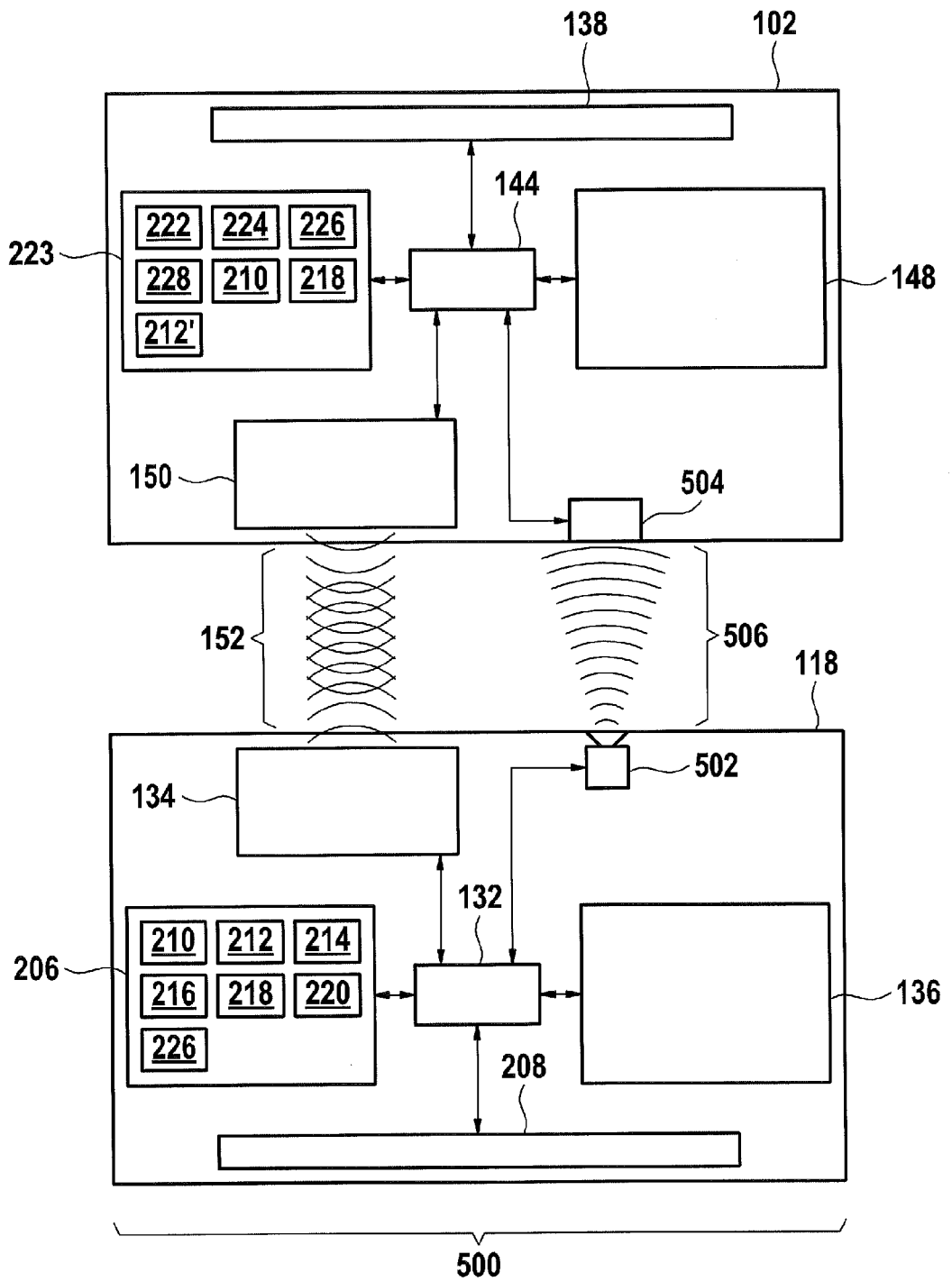
FIG. 5 illustrates a further example of a medical instrument.

FIG. 5 shows a further example of a medical apparatus 500. The example shown in FIG. 5 is similar to that in FIG. 4 except the light has been replaced by a transducer 502. The camera 221 has been replaced by a microphone 504. The transducer 502 is able to transmit sound waves 506 to the microphone 504. In this example the password data 226 is encoded as a sound which can be transmitted from the transducer 502 to the microphone 504 via the sound waves 506 where it is then recorded again and stored as a sound or password data 226. The recording of the password data 226 by the microphone 504 may trigger the processor 144 to initiate the password-authenticated key agreement algorithm 212'.

Figure 6:
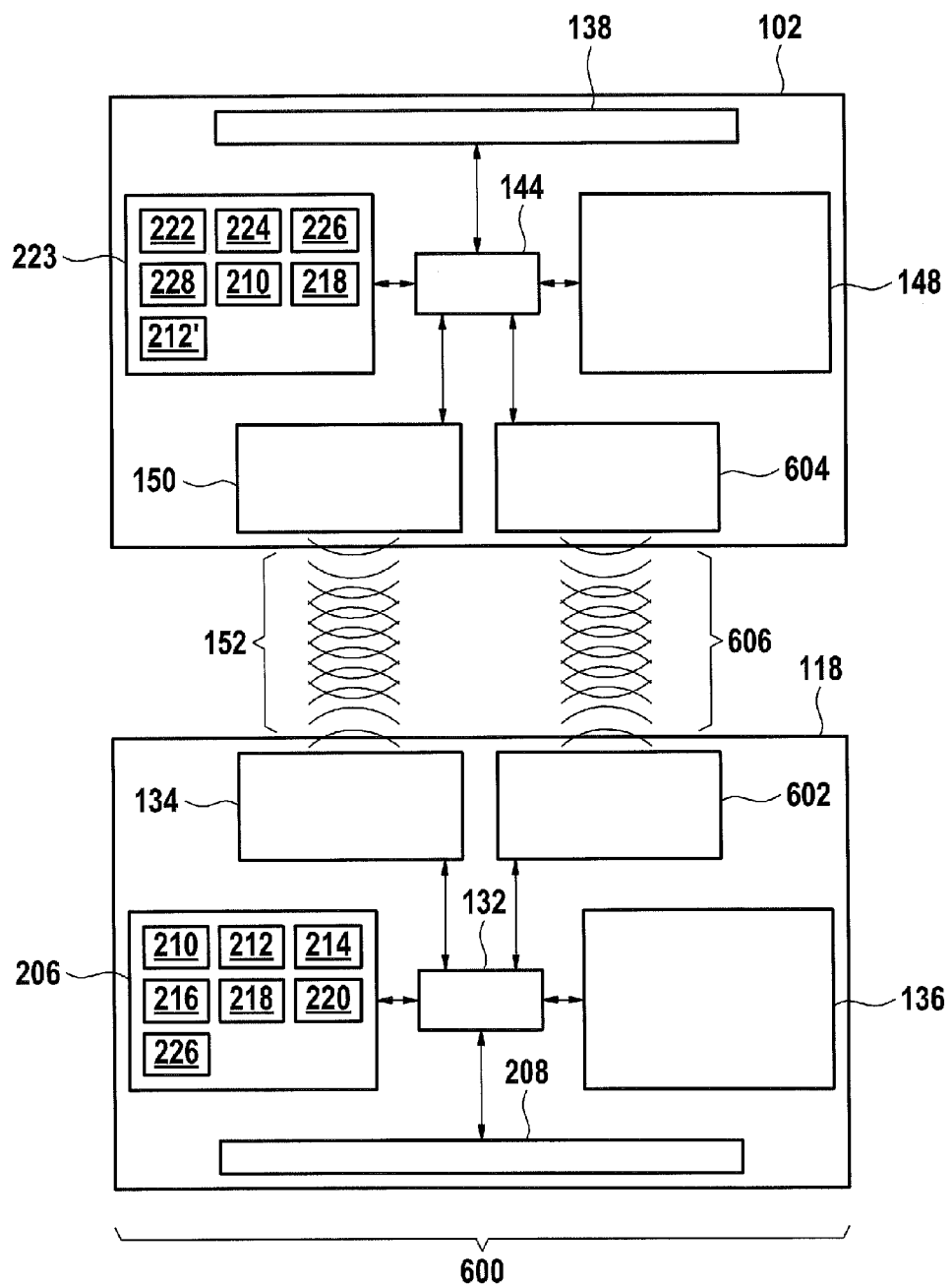
FIG. 6 illustrates a further example of a medical instrument.

FIG. 6 shows a further example of a medical apparatus 600. In this example the medical appliance 104 comprises a first RFID module 602 and the control unit 102 comprises a second RFID module 604. These two RFID modules 602, 604 are able to form an RFID communication channel 606 that is used to exchange the password data 226 or even the onetime password 210 directly via the RFID communication channel 606.

Figure 7:
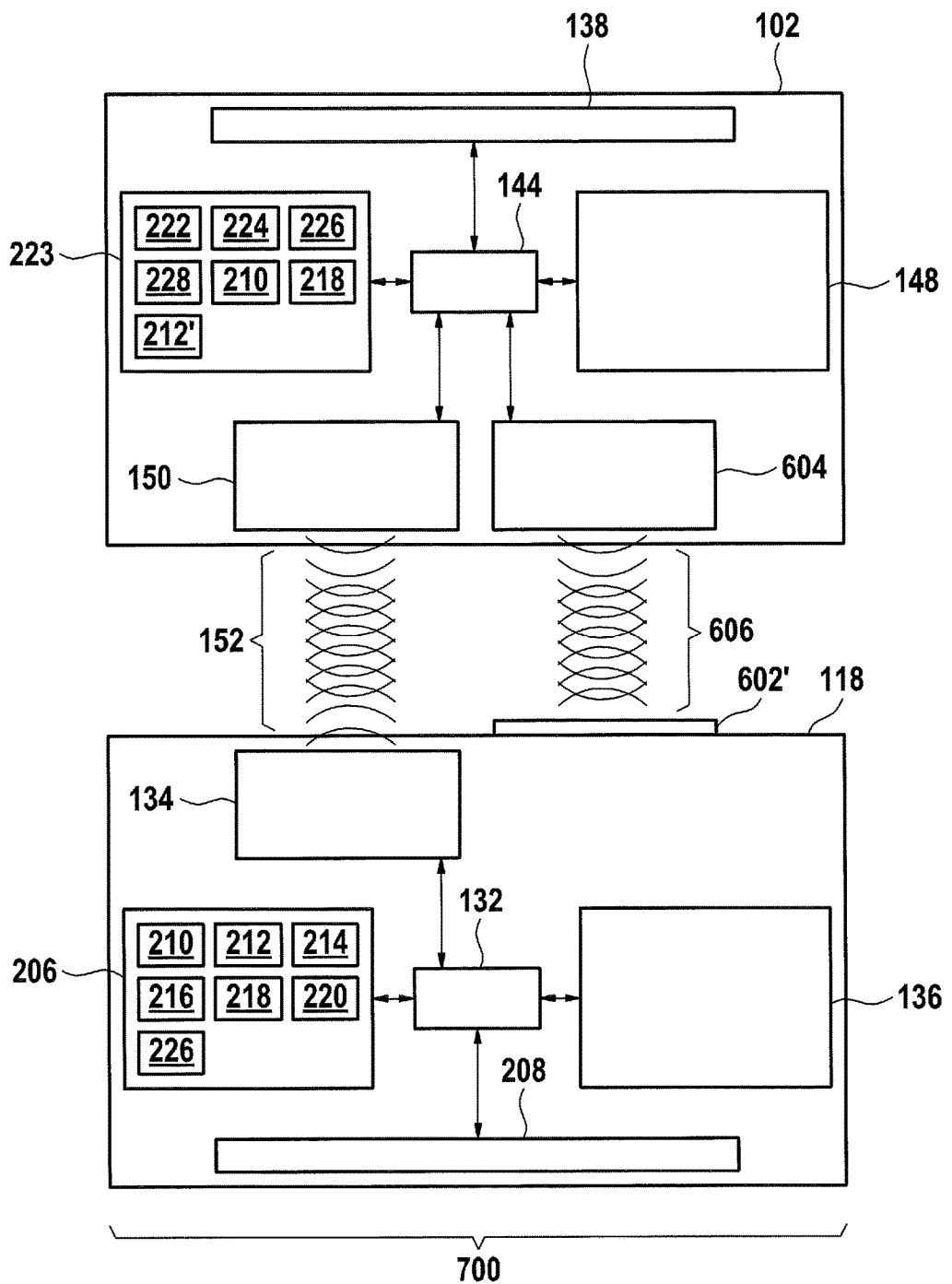
FIG. 7 illustrates a further example of a medical instrument.

FIG. 7 shows a further example of a medical apparatus 700. The example shown in FIG. 7 is similar to that in FIG. 6 except instead of the processor 132 controlling the first RFID module 602 the first RFID module 602' is an RFID tag. The RFID tag 602' will have a separate memory that will store the onetime password or the password data 226 separately from the first memory 206. The second RFID module 604 functions as an RFID reader for the RFID tag 602'.

Standardized communication protocols like Bluetooth allow devices to communicate together. For security reasons it is necessary to be able to recognize specific devices and thus enable control over which devices are allowed to connect to a given Bluetooth device. Available Bluetooth protocols for pairing like secure simple pairing in Bluetooth version 4.0 unfortunately do not protect efficiently against MITM or man-in-the-middle attacks and furthermore require each device to have an input component such as display and/or numeric keypads. The disadvantage of standard Bluetooth available protocols for pairing do not protect against the MITM attacks, especially if one or both the devices did not have an input component as is the case for a patch pump. A patch pump is an insulin pump that is attached to the surface of the subject.

Some example may use a specific combination comprising a password-authenticated key agreement protocol such as J-PAKE having an interface with a standardized Bluetooth low-energy protocol in which the generated high secure random number is stored. A technical solution is the J-PAKE algorithm generates a random number for pairing both devices based on random numbers generated by each device and a password, in this case a onetime password. The password can for example be printed on the medical device for example as a barcode, a 2D code, or dot matrix code and read for example with an integrated camera in the remote controller. The highly secure random number is then integrated into the BLE stack and allows the secure pairing between the medical devices. In addition to J-PAKE other standard protocols may be used. The J-PAKE algorithm may for example be implemented using elliptic curves.

Figure 8:
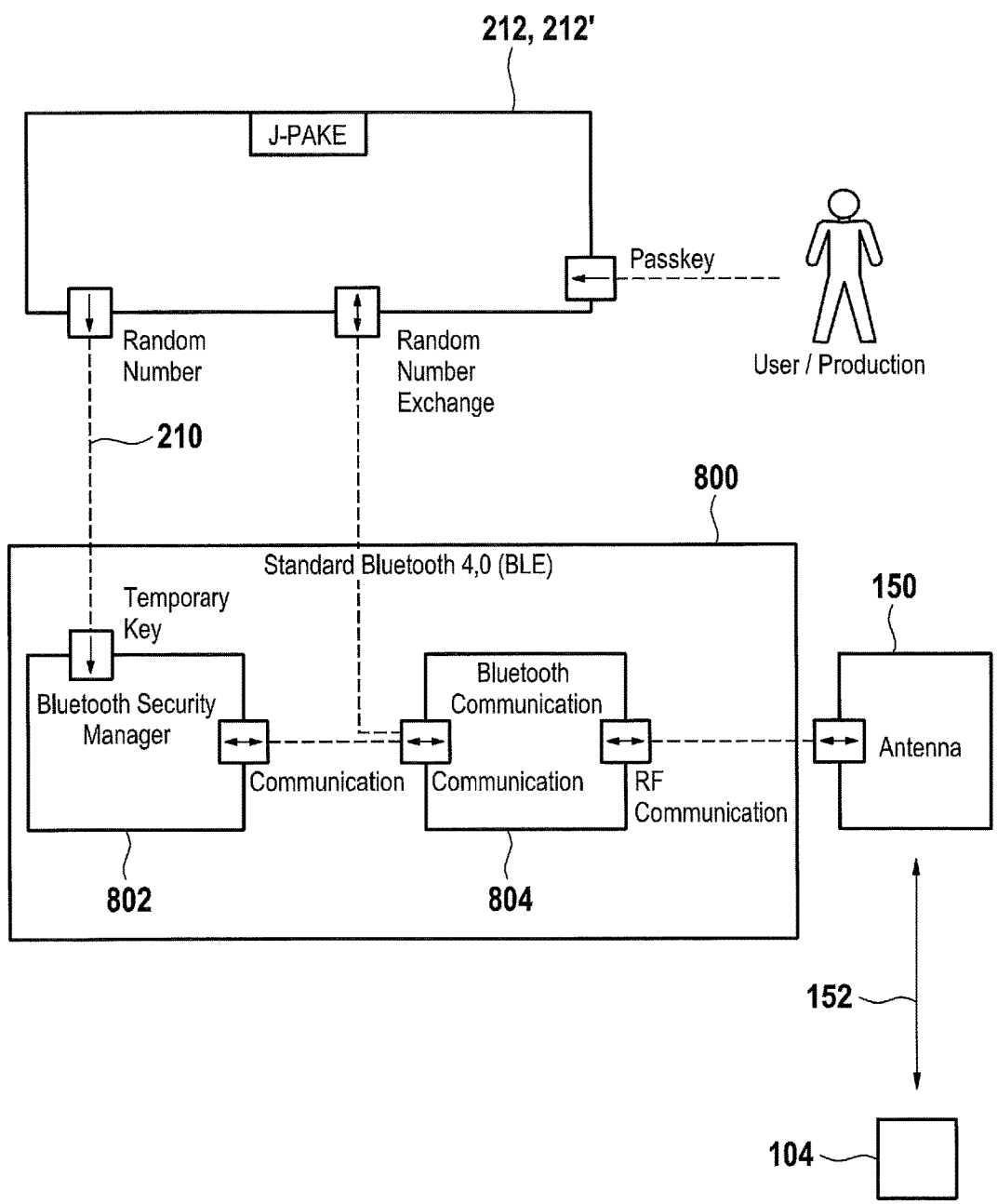
FIG. 8 illustrates the functional relationship of a J-PAKE algorithm and a Bluetooth communication system.

FIG. 8 illustrates how a standard J-PAKE algorithm 212, 212' can be combined with a standard Bluetooth implementation 800. The J-PAKE algorithm 212, 212' supplies a random number or shared secret 210 to the Bluetooth security manager 802. This is then used by the Bluetooth communication module 804 to establish an initial connection 152 which enables the number exchange of the J-PAKE algorithm 212, 212' to exchange random numbers with the medical appliance 104.

FIG. 9 shows a flowchart which illustrates an example of integrating the J-PAKE algorithm 212, 212' with Bluetooth 901. First in step 900 the medical appliance stores a random number 900. Next in step 902 the control unit starts the encryption by sending a message to the medical appliance 104. In step 904 the control unit 102 generates a random number. Next in step 906 the control unit 102 sends a random number to the medical appliance 104. In step 908 the medical appliance sends its random numbers 908 to the control unit 102. After this the medical appliance 104 calculates a Bluetooth encryption key 910. The control unit 912 then also calculates the same Bluetooth encryption key. The password-authenticated key agreement algorithm 212, 212' then passes the Bluetooth encryption key onto the standard Bluetooth algorithm. In step 914 the medical appliance sends the Bluetooth encryption key to the Bluetooth security manager. Also in step 914 the control unit 102 sends its calculated value for the Bluetooth encryption key to its Bluetooth security manager. Next in step 916 the control unit 102 initiates Bluetooth encryption. Next in step 918 the medical appliance 104 sends a parameter for encryption. And finally in step 920 the control unit 102 sends a confirm encryption message to the medical appliance 104. At this point an encrypted Bluetooth communication channel has been established.

LIST OF REFERENCE NUMERALS 100 medical instrument
102 control unit
104 medical appliance
106 cradle
108 adhesive
110 exterior surface
112 subject
114 dermis
116 fatty tissue
118 electronic portion
120 subcutaneous portion
122 pump
124 cannula
126 sensor controller
128 sensor lead
130 sensor
132 processor
134 first Bluetooth communication module
136 first battery
138 touch screen
140 key pad
142 display element
144 second processor
148 second battery
150 second Bluetooth communication module
152 wireless communication channel
200 medical instrument
202 exterior surface
204 machine readable label
206 first memory
208 hardware interface
210 onetime password
212 password-authenticated key agreement algorithm
212' password-authenticated key agreement algorithm
214 control module
216 data log
218 Bluetooth encryption key
220 instructions from Controller
221 camera
222 operating system
223 second memory
224 control application
226 password data
228 password transformation module
300 entering the onetime password into the data entry interface
302 generating a Bluetooth encryption key by the medical appliance and the control unit with the onetime password by exchanging data across the wireless communication channel by executing the password-authenticated key agreement algorithm
304 storing the Bluetooth encryption key in the first memory;
306 disabling the password-authenticated key agreement algorithm in the first memory after storing the Bluetooth encryption key in the first memory;
308 storing the Bluetooth encryption key in the second memory
310 establishing an encrypted Bluetooth communication channel using the first Bluetooth communication module and the second Bluetooth communication module
400 medical apparatus
402 light
500 medical apparatus
502 transducer 504 microphone
506 sound waves
600 medical apparatus
602 first RFID module
602' RFID tag
604 second RFID module (RFID reader)
606 RFID communication channel
700 medical apparatus
800 Bluetooth algorithm
802 Bluetooth security manager
804 Bluetooth communication
806 antenna
900 Store Random Numbers
901 Bluetooth algorithm
902 Start Encryption
904 Generate random number
906 Send Random numbers
908 Send Random numbers
910 Calculate random number for key
912 Calculate random number for key
914 Send key to BLE security manager
915 Send key to BLE security manager
916 Start BLE Encryption
918 Send parameter for Encryption
920 Confirm Encryption

The invention claimed is:

1. A method of operating a medical instrument,
wherein the medical instrument comprises a medical appliance and a control unit, wherein the medical appliance is battery powered by a first battery, wherein the control unit is battery powered by a second battery, wherein the medical appliance comprises an electronic portion and a subcutaneous portion wherein the electronic portion comprises a first processor and a first memory, wherein the first memory contains a onetime password, wherein the first memory further comprises an implementation of a password-authenticated key agreement algorithm;
wherein the control unit comprises a second processor and a second memory, wherein the control unit comprises a data entry interface, wherein the second memory contains the implementation of the password-authenticated key agreement algorithm,
wherein the medical appliance comprises a first Bluetooth communication module,
wherein the control unit further comprises a second Bluetooth communication module, wherein the first Bluetooth communication module and the second Bluetooth communication module are operable for forming a wireless communication channel between the medical appliance and the control unit,
wherein the method comprises the steps of:
entering the onetime password into the data entry interface;
generating a Bluetooth encryption key by the medical appliance and the control unit with the onetime password by exchanging data across the wireless communication channel by executing the password-authenticated key agreement algorithm, wherein the control unit initiates execution of the password-authenticated key agreement algorithm;
storing the Bluetooth encryption key in the first memory;
disabling the password-authenticated key agreement algorithm in the first memory after storing the Bluetooth encryption key in the first memory;
storing the Bluetooth encryption key in the second memory; and
establishing an encrypted Bluetooth communication channel using the first Bluetooth communication module and the second Bluetooth communication module, wherein the encrypted Bluetooth communication channel is the wireless communication channel encrypted using the Bluetooth encryption key.

2. The method of claim 1, wherein the subcutaneous portion comprises a glucose sensor wherein the medical appliance comprises a continuous glucose monitoring system, wherein the method comprises the step of recording a glucose measurement using the continuous glucose monitoring system, wherein the method further comprises the step of transferring the glucose measurement to the control unit using the encrypted Bluetooth communication channel.

3. The method of claim 1, wherein the subcutaneous portion comprises at least one cannula, wherein the medical appliance comprises a pumping system, wherein the pumping system comprises any one of the following: an insulin pump for pumping insulin through the at least one cannula, a glucagon pump for pumping glucagon through the at least one cannula, and combinations thereof; and wherein the method further comprises the step of controlling the pumping system via the encrypted Bluetooth communication channel by the control unit.

4. The method of claim 1, wherein the password-authenticated key agreement algorithm is any one of the following: J-Pake algorithm, EKE, PAK, PPK, SPEKE, Dragonfly, and IEEE standard 802.11-2012.

5. The method of claim 1, wherein the password-authenticated key agreement algorithm is a J-Pake algorithm, wherein disabling the J-PAKE algorithm in the first memory is performed by modifying the J-PAKE algorithm in the first processor such that it does not execute by the first processor once the Bluetooth encryption key has been stored in the first memory.

6. The method of claim 1, wherein the medical appliance has an exterior surface, wherein the exterior surface comprises a label with password data, wherein the password data is descriptive of the onetime password.

7. The method of claim 6, wherein the data entry interface comprises a key pad, wherein the method further comprises the step of entering the onetime password and/or the password data using the key pad.

8. The method of claim 7, wherein the medical instrument further comprises printed matter comprising the onetime password.

9. The method of claim 6 wherein the label is machine readable, wherein the data entry interface is an optical label reader configured for reading the password data, wherein the step of entering the onetime password into the data entry interface comprises reading the password data with the optical label reader, wherein the step of entering the onetime password into the data entry interface further comprises transforming the password data into the onetime password.

10. The method of claim 9, wherein any one of the following: the password data is encoded as a bar code and the optical label reader is a bar code reader,
the password data is encoded as an EAN code and the optical label reader is an EAN code reader, the password data is encoded as a 2 dimensional optical code and the optical label reader is a two dimensional optical code reader, the password data is encoded as a QR code and the optical label reader is a QR code reader, the password data is encoded as a data matrix code and the optical label reader is a data matrix code reader, the optical label reader is a digital camera, and combinations thereof.

11. The method of claim 1, wherein the electronic portion comprises an optical indicator, wherein the data entry interface comprises an optical detector, wherein the step of entering the onetime password into the data entry interface comprises transmitting the onetime password using the optical indicator, wherein the step of entering the onetime password into the data entry interface further comprises receiving the onetime password using the optical detector.

12. The method of claim 1, wherein the electronic portion comprises an audio signal generator, wherein the data entry interface comprises an audio signal detector, wherein the step of entering the onetime password into the data entry interface comprises transmitting the onetime password using the audio signal generator, wherein the step of entering the onetime password into the data entry interface further comprises receiving the onetime password using the audio signal generator.

13. The method of claim 1, wherein the electronic portion comprises a first RFID module, wherein the data entry interface is a second RFID module, wherein the step of entering the onetime password into the data entry interface comprises exchanging the onetime password using the first RFID module and the second RFID module.

14. The method of claim 13, wherein the first RFID module is an RFID tag, wherein the RFID tag comprises an RFID tag memory, wherein the RFID tag memory contains the onetime password.

15. The method of claim 1, wherein the electronic portion comprises a first NFC module, wherein the data entry interface is a second NFC module, wherein the step of entering the password data into the data entry interface comprises exchanging the password data using the first NFC module and the second NFC module.

16. The method of claim 1, wherein the onetime password has lower entropy than the Bluetooth encryption key.

17. The method of claim 1, wherein the step of entering the onetime password into the data entry interface comprises:
  entering password data into the data entry interface, wherein the password data is descriptive of the onetime password; and
  transforming the password data into the onetime password.

18. The method of claim 1, wherein the onetime password is provided to the data entry interface by the medical appliance.

19. The method of claim 1, wherein the medical appliance comprises a serial number, wherein the onetime password comprises at least partially comprises the serial number.

20. A medical instrument, wherein the medical instrument comprises a medical appliance and a control unit, wherein the medical appliance is battery powered by a first battery, wherein the control unit is battery powered by a second battery, wherein the medical appliance comprises an electronic portion and a subcutaneous portion, wherein the electronic portion comprises a first processor (132) and a first memory, wherein the first memory contains a onetime password wherein the first memory further contains an implementation of a password-authenticated key agreement algorithm, wherein the first memory further contains first machine executable instructions,
  wherein the control unit comprises a second processor and a second memory, wherein the control unit comprises a data entry interface, wherein the second memory contains the implementation of the password-authenticated key agreement algorithm, wherein the second memory further contains second machine executable instructions,
  wherein the medical appliance comprises a first Bluetooth communication module, wherein the control unit further comprises a second Bluetooth communication module, wherein the first Bluetooth communication module and the second Bluetooth communication module are operable for forming a wireless communication channel between the medical appliance and the control unit,
  wherein execution of the second machine executable instructions cause the second processor to receive the onetime password into the data entry interface,
  wherein execution of the second machine executable instructions and the first machine executable instructions cause the first processor and the second processor to generate a Bluetooth encryption key by the medical appliance and the control unit with the onetime password by exchanging data across the wireless communication channel by executing the password-authenticated key agreement algorithm, wherein the control unit initiates execution of the password-authenticated key agreement algorithm,
  wherein execution of the first machine executable instructions cause the first processor to store the Bluetooth encryption key in the first memory;
  wherein execution of the first instructions further cause the first processor to disable the password-authenticated key agreement algorithm in the first memory after storing the Bluetooth encryption key in the first memory,
  wherein execution of the second machine executable instructions cause the second processor to store the Bluetooth encryption key in the second memory,
  wherein execution of the second machine executable instructions and the first machine executable instructions cause the first processor and the second processor to establish an encrypted Bluetooth communication channel using the first Bluetooth communication module and the second Bluetooth communication module, wherein the encrypted Bluetooth communication channel is the wireless communication channel encrypted using the Bluetooth encryption key.

21. The medical instrument of claim 20, wherein the first processor disables the password-authenticated key agreement algorithm in the first memory by deleting or overwriting at least a portion of the password-authenticated key agreement algorithm in the first memory.

* * * * *